(12) United States Patent
Tiemann et al.

(10) Patent No.: US 6,190,348 B1
(45) Date of Patent: Feb. 20, 2001

(54) DISPOSABLE APPLICATOR

(76) Inventors: Harris A. Tiemann, P.O. Box 816; Phillip D. Sharp, P.O. Box 366, both of Clayton, OK (US) 74536

( * ) Notice: Under 35 U.S.C. 154(b), the term of this patent shall be extended for 0 days.

(21) Appl. No.: 09/315,888

(22) Filed: May 20, 1999

Related U.S. Application Data

(63) Continuation of application No. 09/017,178, filed on Feb. 2, 1998, now abandoned, which is a continuation-in-part of application No. 08/630,636, filed on Apr. 10, 1996, now abandoned.

(51) Int. Cl.[7] .............................. A61F 13/20; A61F 9/02
(52) U.S. Cl. ................. 604/15; 604/288; 604/60
(58) Field of Search ................. 604/11–18, 904, 604/285–288, 57–60

(56) References Cited

U.S. PATENT DOCUMENTS

| | | | |
|---|---|---|---|
| 3,297,031 | * | 1/1967 | Bray ........................................ 604/15 |
| 3,753,437 | * | 8/1973 | Hood et al. ............................. 604/15 |
| 4,822,332 | * | 4/1989 | Kajander ................................ 604/16 |
| 5,395,308 | * | 3/1995 | Fox et al. ............................... 604/15 |

* cited by examiner

Primary Examiner—Dennis Ruhl
(74) Attorney, Agent, or Firm—Molly D. McKay

(57) ABSTRACT

A disposable applicator for implanting medicaments of various kinds into the human body without exposure of either the user or the recipient to pathogens of the other, and without exposure of either to latex rubber proteins. Differing variants may be sized variously for infants, children and adults, with various stop means for preventing insertion beyond a desired distance. In addition, other variants are particularly suited for use by untrained personnel or by persons with physical conditions which restrict their range of motion. A particularly preferred variant is sufficiently flexible so as to conform to body contours, thereby neither destroying nor irritating possibly sensitive skin tissue.

15 Claims, 3 Drawing Sheets

DISPOSABLE APPLICATOR

This application is a continuation of U.S. application Ser. No. 09/017,178 filed Feb. 2, 1998, now abandoned, which in turn was a continuation-in-part of then U.S. application Ser. No. 08/630,636 filed Apr. 10, 1996, which was abandoned upon filing related application 09/017,178, and which specifically enumerated prior applications are hereby incorporated by reference.

BACKGROUND OF THE INVENTION

This invention relates to disposable applicators suitable for use by trained personnel in hospital or other institutional environments; by untrained persons at home, both for self-administation and for use on small children; and for use by those having severe restrictions on their freedom of movement. It has important benefits in the prevention of disease transmission, in reducing a serious and increasing health hazard to health professionals, in reducing the risks of injury to small children, and in helping the handicapped live independently.

Insofar as applicants can determine, there are no disposable suppository applicators on the market today, and certainly none in widespread use. Due to the costs and uncertainties of sterilization procedures, there likewise appear to be no applicators on the market intended for repeated use. Indeed, in the present state of the health care industry, it is virtually certain that no such applicators would be used repeatedly by health care personnel, even if they were available. The industry has, instead, turned to other means of providing protection for its personnel, primarily the latex glove.

However, use of the latex glove has proved in practice to be far from the panacea originally envisioned by health care planners. It has long been known that even an apparently perfect latex glove can have minute openings too small to be seen by the human eye yet large enough to allow the HIV or other virus molecules to pass through. In May of 1988, the National Institute for Occupational Safety and Health issued a report on the effectiveness of rubber latex gloves as a barrier to human immuno-deficiency virus in which it stated that it was evident that standard medical rubber latex gloves are ineffective in providing reliable barriers against many pathogens, and that plastic medical gloves were no better. The NIOSH report further pointed out that the prevalence rate for AIDS cases with no identified cause among health care workers was nearly twice the rate among all other AIDS patients. As the possibility of transmission of and infection by such viruses becomes more widely known, more and more health care workers are turning to the use of double pairs of latex gloves, as recommended by the CDC. However, not only does this double the cost of such prophylactic measures, but even this extreme step can still fail to adequately protect the wearer, and the use of latex itself can actually cause its own unique problems.

Being a natural product, the latex in such gloves can and all too often does cause allergic reactions. The American College of Allergy, Asthma and Immunology has estimated that at least as many as eight to seventeen percent of all health care workers are latex-sensitive; others have estimated that as many as one in five may exhibit various degrees of sensitivity to the natural protein comprising latex. The range of allergic reactions runs from skin rash, hives, intense itching, swollen eyes, runny noses and sneezing to asthma-like symptoms including wheezing, coughing and shortness of breath, and can progress to inflamed mucous membranes and closed airways as anaphylactic shock develops.

Several deaths have been confirmed among health care workers to have resulted from latex allergies, and the Food and Drug Administration has reported at least sixteen deaths due to anaphylactic shock caused by allergic reactions to but one type of latex devices, enema catheters.

Many health care professionals have formed the opinion that the powder commonly employed in latex gloves to make it easier to don and doff the gloves, particularly after perspiring, is the primary cause of such problems. According to this theory, some of the natural protein molecules in the latex glove bind to the powder, and the protein-based powder then becomes airborne when the gloves are removed, where they are subsequently inhaled by the workers. At least one state, Oregon, has considered statutorily banning the use of all powdered latex gloves in health care facilities.

However, not even powder-free latex gloves can solve the problem which applicants' present invention solves, nor so conveniently. The FDA, in June of 1996, issued a Public Health Advisory to the effect that not only could large quantities of non-powdered, chlorinated latex gloves spontaneously ignite in warehouse conditions, but that merely exposing the gloves to warmer temperatures could cause the latex to deteriorate and lose its effectiveness as a barrier. And, of course, even an apparently perfect, non-powdered latex glove can still have microscopic pores large enough to permit the passage of even the relatively large HIV virus.

It is thus apparent that a serious medical problem exists for health care providers in the aggregate, and has been known to exist for quite some time. It is also apparent that the industry is in urgent need of devices such as applicants' which eliminate a major need for doubled latex gloves while positively preventing the transmission of disease.

Various types of devices are known to the art for implanting different kinds of materials or fluids into the body, but which for various reasons do not accomplish the purposes of the present invention. The type of devices known as catheters generally are, comparatively speaking, very expensive devices whose relatively high cost can be justified either by the worth of the procedure or by a replacement cost sufficiently great to justify the cost of sterilization for re-use. Further, devices of this type typically are little more than elongated, flexible, covered hypodermic needles intended to be threaded up a vein or artery to deliver the material or fluid to a pre-selected location far removed from the point of entry. U.S. Pat. No. 4,900,303 to Lemuelson may be representative of this class. Lemuelson—and other catheter patents—disclose little of interest for the purposes of this invention beyond finger rests for control and plunger mechanisms for dispensing the materials or fluids.

The class of devices known as sample collecting devices, although intended for a purpose opposite that of the present invention, may be considered intermediate between catheters and the present invention. Generally, such devices are not intended for sampling at locations so far removed from the point of insertion, and recently a sub-class of such devices intended for self-use has appeared. U.S. Pat. No. 4,877,037 to Ko and Fanselow, and the patents disclosed therein, may be representative of this class. Ko discloses a washerlike guard means slideably adjustable among an unlimited number of positions along a protective sleeve, and necessarily relies upon a precise relationship of sizes to permit the precisely desired, tight frictional fit. Ko also discloses a separate stop means which may be a discrete piece also relying on a precise frictional fit or in at least one embodiment may be formed integrally with its respective tube at one specific position. Being intended for single uses and to eliminate the costs of trained medical personnel, such devices can in general be both more precisely made and more expensively made than can devices which are made for the purposes of the present invention.

U.S. Pat. No. 939,693 to Holtzmann discloses a device also intended for placement of suppositories and bulk 'semi-plastic' medicaments. The Holtzmann device comprises a slotted outer tube with a flat-surfaced or washer-like flange rigidly attached to its outer end, an inner tube open at both ends and telescopically slidable within the outer tube, and a piston interior to the inner tube. The end of the outer tube opposite the open end is operably closed by a threaded plug mating with oppositely-machined threads on the interior side of the outer tube, and a pin or screw is attached at one end to the inner tube and projects through the slot in the outer tube and is attached at its other end to a slidable ring or sleeve encircling the outer tube. Use of the device is described as requiring two hands to extend the inner tube into position for receiving either medicaments or discrete suppositories; after placement, a suppository is dispensed in another two-handed operation by holding the outer tube and flange stationary with one hand while withdrawing the inner tube with the other hand by means of the slidable sleeve, during the course of which the stationary piston prevents the suppository from remaining inside the inner tube. The disadvantages of such a complicated device are readily realized: prohibitively expensive for today's manufacture for single usages; impossible to (economically) sanitize for repeated usages; and two-handed operations required both to initially adjust the device to receive a suppository and to dispense the suppository. Thus devices of this type are incapable of achieving the purposes of this invention.

Italian Patent No. 580,657 represents yet another approach. Like Holtzmann, it too has an outer tube with a threaded end cap, although with such on the outer rather than the inner surface of such tube. The outer tube has an integral, fixed position flange, undoubtedly serving as a rest or stop. As shown in the drawings, the end-cap is formed with an enlarged rim and a central orifice for receiving a plunger connected at its exterior end to a relatively large disc and at its other end to a moveable piston inside the outer tube. From the drawings, operation would appear to require forcing a portion of a suppository into the open end, thereby leaving most of the suppository exposed during insertion, permitting premature melting, breakage and associated difficulties. Although actual dispensation may be accomplishable with one hand, presumably with two fingers on the far side of the enlarged rim of the end cap and a thumb on the opposite side of the plunger disc, such a device obviously has some of the same disadvantages as the Holtzmann-type devices, namely, expense of manufacture and difficulty and cost of sterilization, as well as the additional disadvantage of inability to protect suppositories during the insertion process.

Since none of these prior devices appears capable of solving the problems solved by the present invention, it is not surprising to see that apparently neither of these types of devices is on the market today, nor, for that matter, to the best of applicant's ability to ascertain, is any other suppository insertion device, of any kind. Thus, despite the accentuated need caused by the extreme problems of AIDS and latex allergies and reactions, the longstanding need for a product such as applicant's remains unfilled. In addition, should the present invention be widely adopted, then numerous instances of latex reactions and of disease transmissions will have been prevented.

OBJECTS OF THE INVENTION

It is therefore a principal object of the present invention to eliminate a significant source of latex reactions among health care providers in hospitals, nursing homes and home care situations, and among health care recipients.

It is another object of the present invention to eliminate a significant source of transmission of disease to health care providers, whether in institutions or in the home.

It is yet another object of the present invention to provide an applicator inexpensive enough to be disposable after but one use, thereby avoiding the cost, time and risks of attempting sterilization procedures.

It is yet another object of the present invention to provide an applicator which can be safely used by untrained or inexperienced personnel, or by persons whose physical conditions restrict their range of motions.

It is still another object of the present invention to provide an applicator which will be neither destructive of nor irritating to skin tissues.

These and other objects will be apparent to those skilled in the art upon careful consideration of the teachings herein.

SUMMARY OF THE INVENTION

A preferred embodiment of the present invention will accomplish several functions simultaneously. That is to say, while all embodiments will eliminate the need for latex gloves while preventing disease transmission even more effectively than such gloves, some preferred embodiments will also accomplish still other purposes, such as being suitable for use by untrained personnel or for self-administration administration by persons with restricted range of motions. These and other purposes are readily accomplished with the flexible version of the preferred applicator, some embodiments of which may incorporate a bellows section intermediate the ends or a plurality of scorings to provide the preferred degree of flexibility. Flexing is further facilitated by the employment of a thin flexible shaft interior to the applicator and connecting the dispensing end and a thumb rest at the opposing end. While the flexible version is shown for simplicity with the frictional fit mode for the stop means for preventing unwanted depth of insertion, it is preferred for all versions to incorporate one of the more positive means for securing the stop means in place as is shown on the non-flexible version. This feature is particularly desirable for use with infants or small children, and others with particular sensitivity.

DETAILED DESCRIPTION OF THE PREFERRED EMBODIMENT

Figure 1:
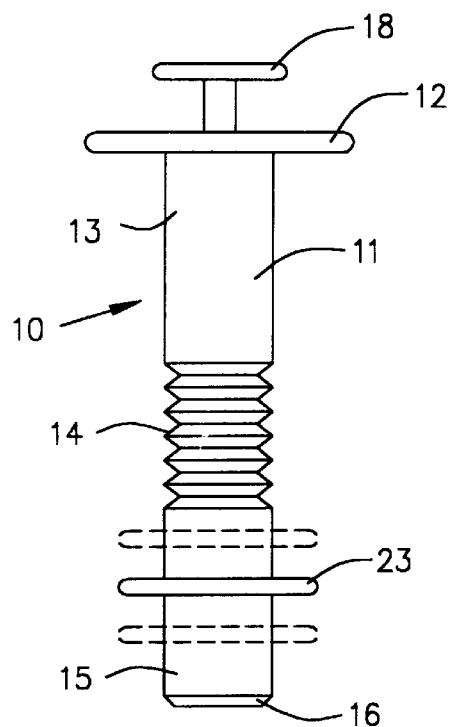
FIG. 1 is a side view of one embodiment of the present invention with a bellows section intermediate the suppository-receiving portion of the device and the finger and thumb rests portion. The frictional fit version of the optional depth stop means is also illustrated in this drawing.
Figure 3:
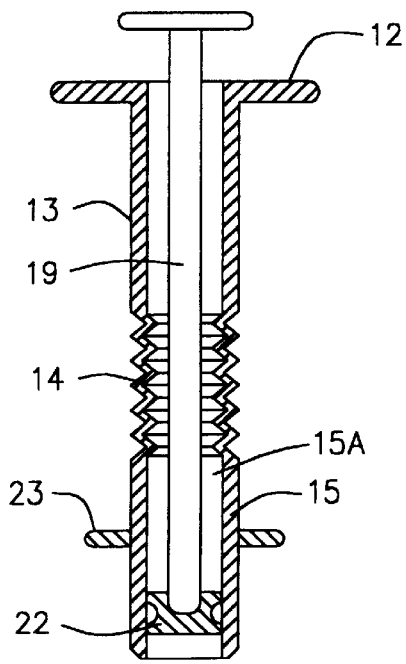
FIG. 3 is a side view in partial cross-section of the embodiment shown in FIG. 1, i.e., it is a cross-sectional view of the body and stop means but not of the plunger means.
Figure 10:
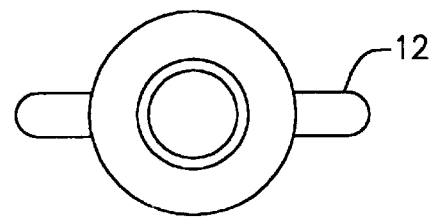
FIG. 10 is a top view of the device as shown, for example, in FIG. 1.

FIG. 1 is a side view of one preferred embodiment of the present invention. It is characterized generally by an applicator 10 having a body 11 in turn having in this embodiment, five sections 12–16. At the top of body 11, of the views as shown in FIGS. 1 and 3, is an enlarged portion 12, preferably formed integrally with the remainder of the body, for ease of securing with but two fingers when in use. Although this enlarged portion 12 could be circular or elliptical, material will be saved, and packaging and distribution costs lowered, if portion 12 is configured as shown in FIG. 10. Section 13 of the applicator body may more conveniently be of the same size and configuration as the lower portion of the applicator, i.e., sized to receive conventional suppositories. Section 13 is preferably formed integrally with the enlarged portion 12 and the remaining sections 14, 15.

Section 14 is depicted in this embodiment as a bellows section intermediate upper portion 13, which may be thought of as the control portion, and lower portion 15, which may be referred to as the suppository receiving portion. The lower end 16 of section 15 is preferably tapered or rounded to eliminate the sharp edge which would otherwise be present were the end portion flat and perpendicular to section 15 as is conventionally done. Although more expensive to construct, such an arrangement is particularly preferable for infants and small children, for persons with weakened blood vessels, and for all others for whom the irritation of a scraping edge may prove to be deleterious.

As shown in FIGS. 1 and 3, bellows section 14 is depicted in this embodiment with five accordion-type pleats circumferentially formed around the body. Although such section may be formed with more or fewer such pleats, in general three to five such pleats are preferable. Fewer pleats will restrict the range of movement and force the flexible shaft to bend in a tighter radius of curvature; more pleats will minimize the degree of bend forced upon each individual pleat and reduce the chance of breakage, as well as increase the radius of curvature forced upon the flexible shaft.

It is to be understood that devices of the present invention may be sized differently for different applications. Thus infants and small children may utilize the smallest device, and adults the largest. A convenient length for the adult sized, non-flexible version may be four inches, while a convenient length for the flexible version may be on the order of six inches. For either version, the diameter of the receiving end may be on the order of a half inch, with 0.515 inch being preferred. Cylinder wall thickness of approximately 1/32 inch will be both adequately sturdy yet flexible enough to accommodate the requisite degree of bending for the scored version, while a wall thickness on the order of half that magnitude may be preferable for bellows section 14. Enlarged portion 12 need be only large enough for the fingers to support the applicator while the thumb presses in the opposite direction; although this member may be of any convenient size, a transverse dimension on the order of one-half inch, i.e., beyond the body of the applicator in either direction, FIG. 10, is preferred.

Below bellows section 14 is situated the suppository receiving end 15 of the applicator, preferably with the aforementioned tapered or rounded edge 16. It is desirable to have a length for suppository receiving end 15 sufficient to permit the plunger to be retracted adequately to fully receive the suppository without the dispensing end of the plunger engaging any portion of bellows section 14. So doing will insure that the dispensing end will not encounter any of the recesses internal to the bellows section and require additional force to free the dispensing end of the plunger. Body 11 of applicator 10, comprising sections 12–16, is preferably formed as a single unit.

Figure 5:
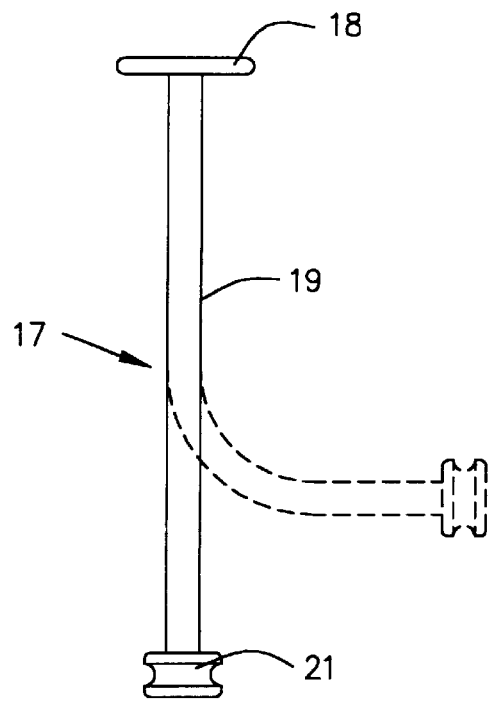
FIG. 5 is a side view of one embodiment of a preferred plunger means, i.e., with a flexible shaft.

Interior to body 11 is the actual dispensing means 17, shown formed preferably as a plunger and most clearly in FIG. 5. Dispensing means 17 may be seen to preferably comprise three sections, a thumb support section 18 and flexible shaft means 19 connecting said thumb support section to a dispensing end 21. For suppository use dispensing end 21 need not form a seal with the interior surface 15a of receiving portion 15, and virtually any shape of dispensing end 21 may be employed as such materials are quasi- or semi-solid. If intended for use with other medications less solid, such as Preparation H®, then a dispensing end 22 formed and shaped to more nearly provide a seal is preferred, as is illustrated in FIG. 3. Forming the dispensing end 22 in a shape and of a size to approximately fit and approximately seal the interior of receiving portion 15 will permit any given applicator to serve in a dual capacity.

One form of stop means 23 is shown in FIG. 1 circumferentially surrounding lower portion 15 of body 11, a frictional fitting stop means. To use the embodiment of the present invention as depicted in FIG. 1, one would retract the plunger by pulling back on thumb support means 18 sufficiently to receive, preferably completely, the intended suppository, slide the frictional fitting stop means 23 to the desired position, and insert the applicator. Any errors in alignment will automatically be compensated for by the bending of flexible bellows section 14 of FIG. 1 as required. If the user experiences restrictions on his or her movements, flexible section 14 can be pre-adjusted to whatever angle may be preferable for the individual user.

Figure 2:
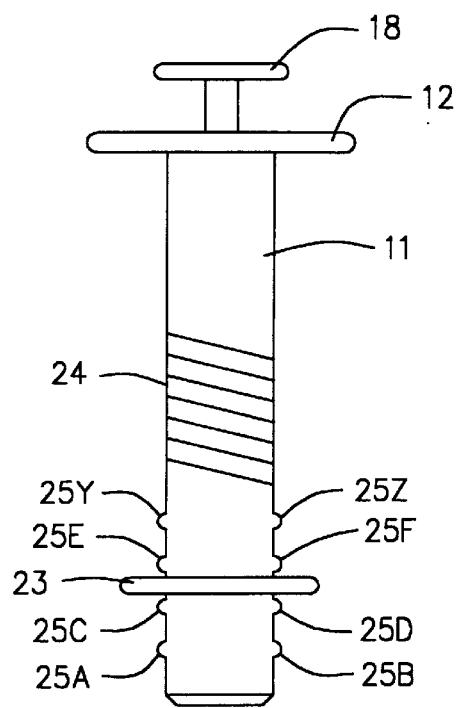
FIG. 2 is a side view of another embodiment wherein the flexure feature is provided by a plurality of scorings instead of a bellows section. This version may be preferable whenever the full range of displacement or bending provided by the bellows version is not required. Also disclosed in FIG. 2 is a plurality of protrusions on the body of the applicator for securing the optional stop means in position.
Figure 4:
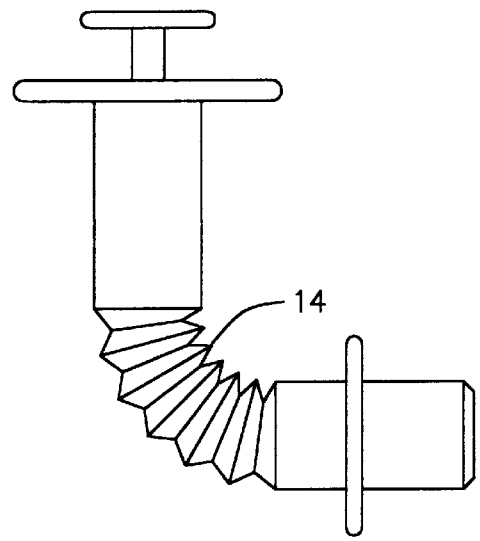
FIG. 4 is a side view of the embodiment of FIG. 1 illustrating an extreme displacement of the device.

FIG. 2 is similar to FIG. 1 except that flexible bellows section 14 is shown as replaced by flexible scored section 24 and a different arrangement for positioning the adjustable stop means 23 is employed. It should be understood that the device depicted in FIG. 2 is intended for applications in which the degree of bending required is less than that required for the device of FIG. 1. Indeed, as shown in FIG. 4, the invention as depicted in FIG. 1 may easily accommodate a 90° bend, or even more.

Figure 6:
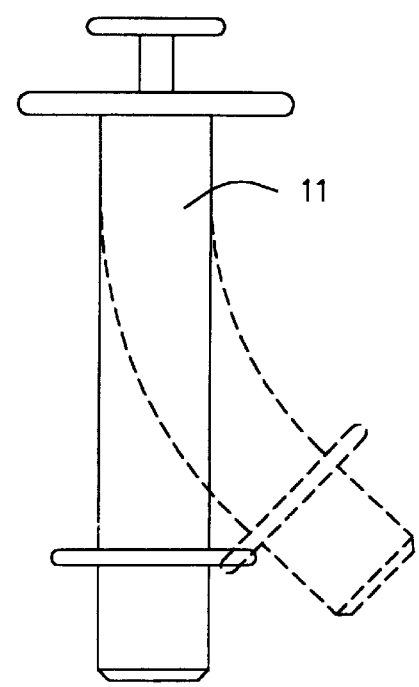
FIG. 6 is a side view of a non-flexible version of the preferred applicator employing grooves to more securely position the optional stop means. With this variant, an extremely tight frictionally-fitting stop means may be employed, which will 'relax' in a selected groove, or a stop means of the type displayed in FIG. 7 may be utilized.

Other applications requiring less bending or flexibility may also be fulfilled by the embodiment depicted in FIG. 6. In this embodiment, the requisite degree of flexibility of body 11 may be achieved by constructing the body out of sufficiently thin and/or resilient plastic as to permit the desired degree of deformation to be achieved.

Also shown in FIG. 2 is a plurality of protrusions preferably formed integrally with lower section 15 of body 11. It may be observed that such protrusions are depicted in sets of two, spaced apart approximately 180° circumferentially on lower section 15. Thus protrusions 25a, 25b would form one set; protrusions 25c, 25d another set, etc. While it is preferable to employ such protrusions in sets of at least two, it is not essential; one such protrusion will serve to positively and mechanically prevent one side of stop means 23 from being pushed back too far during use, while the degree of motion permitted the other side of said stop means will depend upon the degree of slackness or amount of space between the size of the orifice of stop means 23 and the outer diameter of lower portion 15. This is to say, a tight-fitting stop means 23 will be held nearly perpendicularly by just one protrusion, while a loose-fitting stop means will be free to take on an angular position other than perpendicular, which may be a separately desirable feature in some instances.

It also should be observed that the series of sets of protrusions (25a, 25b), (25c, 25d), etc., provide only a limited number of fixed positions from which to choose, and that the protrusions (25y, 25z) which form the last set are preferably larger than the others. That is to say, it is preferred to have the last set of protrusions be large enough to prevent stop means 23 from being forcible over such protrusions, thus providing a means for positively preventing insertion to too great a depth. If protrusions 25 are provided in pairs, then it is desirable to have sufficient space between the orifice of member 23 and lower body 15 such that stop means 23 can be forced over each protrusion of a pair, such as 25a, 25b, one at a time rather than simultaneously, in order to require less force to adjust the stop means to the desired pre-selected position.

The sets of protrusions may be any desired shape; the sizes will depend to some extent upon the spacing between stop member 23 and lower body 15. Such protrusions may conveniently be hemispherical or of other convex shape, and may be on the order of 0.015 inch in diameter and/or height. The final protrusions 25y, 25z, which serve as positive stops, may be on the order of 0.050 inch in diameter and/or height. Alternatively, such protrusions may be presented in sets greater than twos, and alternate rows may be staggered as desired, but pairs appear both adequate and preferable for most applications. A first row of protrusions 25a, 25b at approximately 1.5 inches up from the lower end 16 of body 11, with incremental placements back to about 2 inches, will allow suppositories to be inserted to depths of 1.5 to 2 inches. Alternatively, each pair of protrusions could be replaced with a ring extending all the way around the circumference of lower body 15, or with a plurality of partial rings, but such would seem to be the functional equivalent of the discrete protrusions as illustrated in FIG. 2, and would require greater force to adjust the depth stop to the desired location.

Figure 8:
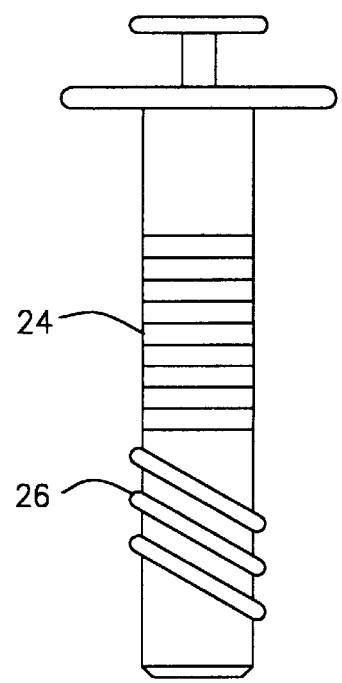
FIG. 8 is a side view of one embodiment of the present invention.
Figure 9:
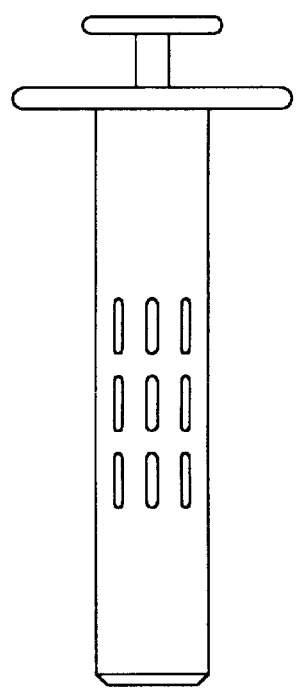
FIG. 9 is a side view of still another embodiment of the present invention with an alternative means for permitting flexure. Stop means have been omitted for clarity.

A preferable alternative is the embodiment shown in FIG. 8. In this embodiment, instead of a plurality of rings to secure stop means 23, a ring in the form of a continuous spiral 26 circumscribes lower body 15 in the area of interest. Such an arrangement may be readily seen to provide a more positive stop than the pure frictional fit, while being easier to use than the versions which require 'snapping' or deforming the stiff but yieldable means 23 over protrusions 25 or over circular or partially circular rings, an advantage which may be of significant benefit to the physically impaired. Those skilled in the art will appreciate that the embodiment of FIG. 8 will allow an impaired user to readily, and easily, adjust the stop means to the desired location. It will be further appreciated that this embodiment can be combined with any of the upper versions, i.e., with the fully deformable bellows variant, the non-deformable variant, or any intermediate variant.

Figure 7:
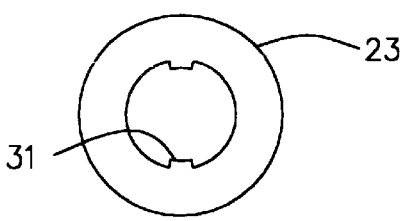
FIG. 7 is an end view of a preferred version of stop means of the type having a protrusion to positively and mechanically lock the stop means in a desired position.

If desired, a series of indicators, such as recesses or protrusions, could be formed into the spaces between successive rotations of the spiral, and an indicator 31 formed in the orifice of stop means 23, as exemplified in FIG. 7, so that successive rotations could more readily be ascertained by successive clicks as the indicator of the orifice engaged each indicator within the spiral spaces, and so that the rotatable stop means could be held in position more securely. As such engagements would be (locally) longitudinal rather than transverse, the indicators could easily be sloped so as to minimize the force required to disengage each successive indicator. In any event, as a safety precaution, the upper end of the spiral upset is preferably closed to prevent the stop means from being positioned at too great a depth.

Figure 11:
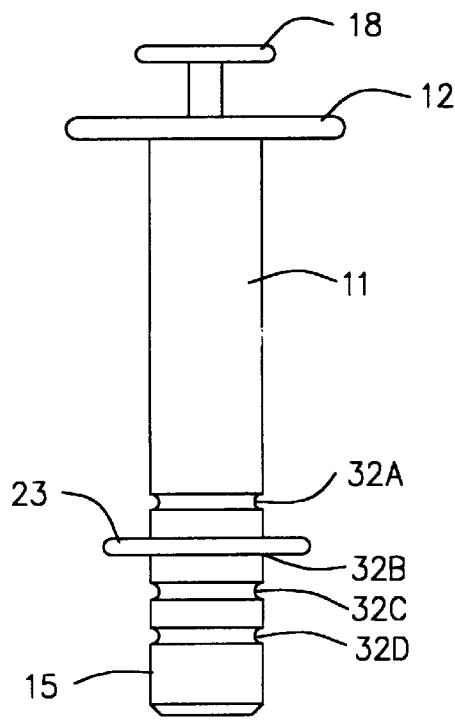
FIG. 11 is a side view of yet another embodiment.

Yet another embodiment is displayed in FIG. 11. Continuous recessions in the form of grooves 32a, 32b, 32c and 32d circumscribe the lower portion 15 of the exterior surface of body 11, and are particularly suited to interact with the interior of the orifice of stop means 23 to positively and mechanically lock said stop means into a desired position. It may be seen from FIG. 11 that said stop means is illustrated as occupying groove 32b. If stop means 23 produces a sufficiently tight fit with lower portion 15 of body 11, then the dual-purpose indicator/locking means 31 of FIG. 7 may not be needed. This is to say, a sufficiently tight stop means 23 will "relax" into each successive groove 32a, 32b, etc. so as to hold said stop means in place. However, it is preferred, for use by the blind or others with high degrees of visual impairment, to utilize the arrangement depicted in FIG. 7 with the recessed grooves depicted in FIG. 11. So doing not only will provide a clear, audible signal as the protrusions 31 'snap' into each successive groove, thereby making it easier for the visually impaired to know the setting, but will also permit the manufacturing tolerances to be relaxed substantially.

Although the recessions 32a–d are illustrated in FIG. 11 as continuous, it is only preferred and not essential that they be continuous. Instead of a series of discrete recessions as illustrated in FIG. 11, stop means 23 could be easily positioned in a spiral-oriented groove, the base of which could have, spaced along the locally-longitudinal groove, a series of discrete surfaces complementary to the protrusion 31 of stop means 23. This is to say, such discrete surfaces could be in the form of rectangular recessions sized to accommodate protrusions 31, but with sloped ends to ease entry and exit of protrusion 31 into such recessions. Alternatively, such discrete, complementary recessions could be replaced by small, discrete protrusions spaced along the base of the spiral groove to provide a similar indicating/holding function. Either of such variations would be a considerable assist to the visually impaired.

Thus, the present invention discloses novel apparatus which will not only prevent the spread of disease to health care workers and eliminate the problems caused by latex protein allergies, but apparatus which is well suited for use with small children and for self-administration, including those with limited mobility, impaired vision, or even blindness Still other alternate forms of the present invention will suggest themselves from a consideration of the apparatus and practices hereinbefore disclosed. Accordingly, it should be clearly understood that the devices and techniques described in the foregoing explanations and depicted in the foregoing drawings are intended as exemplary embodiments of the invention and not as limitations thereto.

What is claimed is:

1. A disposable suppository medicament applicator comprising:

an applicator body having a plunger barrel formed therethrough from a plunger end thereof to a suppository receiving cavity formed at an insertion end thereof; and a plunger member having a flexible shaft, said flexible shaft having a plunger bulb secured to a first end of said flexible shaft and a thumb rest formed at a second end of said flexible shaft, said plunger bulb being sized to sealingly, slidingly contact a sidewall defining said suppository receiving cavity;

said applicator body including a flexible bellows section having a plurality of circumferential accordion pleats formed therein in a manner to allow the position of said insertion end with respect to said plunger end to be adjusted by bending said bellows section to a desired angle.

2. The disposable applicator of claim 1, wherein said applicator body further includes a plunger section; and each of said plurality of accordion pleats is independently collapsible and expandable in a manner to allow said bellows section to be bent with respect to said plunger section.

3. The disposable applicator of claim 1, wherein said insertion end has a beveled tip portion.

4. The disposable applicator of claim 3, wherein said applicator body further includes a plunger section; and each of said plurality of accordion pleats is independently collapsible and expandable in a manner to allow said bellows section to be bent with respect to said plunger section.

5. The disposable applicator of claim 1, wherein said plunger end has two integrally formed finger flanges extending outwardly from a terminal portion thereof.

6. The disposable applicator of claim 5, wherein said insertion end has a beveled tip portion.

7. The disposable applicator of claim 6, wherein said applicator body further includes a plunger section; and each of said plurality of accordion pleats is independently collapsible and expandable in a manner to allow said bellows section to be bent with respect to said plunger section.

8. The disposable applicator of claim 5, wherein said applicator body further includes a plunger section; and each of said plurality of accordion pleats is independently collapsible and expandable in a manner to allow said bellows section to be bent with respect to said plunger section.

9. The disposable applicator of claim 1, further comprising:

an insertion depth stop, constructed from a resilient material, positionable by a user on said insertion end and held in place by a resilient, frictional gripping force from said resilient material.

10. The disposable applicator of claim 9, wherein said insertion end has a beveled tip portion.

11. The disposable applicator of claim 9, wherein said applicator body further includes a plunger section; and each of said plurality of accordion pleats is independently collapsible and expandable in a manner to allow said bellows section to be bent with respect to said plunger section.

12. The disposable applicator of claim 9, wherein said plunger end has two integrally formed finger flanges extending outwardly from a terminal portion thereof.

13. The disposable applicator of claim 12, wherein said applicator body further includes a plunger section; and each of said plurality of accordion pleats is independently collapsible and expandable in a manner to allow said bellows section to be bent with respect to said plunger section.

14. The disposable applicator of claim 12, wherein said insertion end has a beveled tip portion.

15. The disposable applicator of claim 14, wherein said applicator body further includes a plunger section; and each of said plurality of accordion pleats is independently collapsible and expandable in a manner to allow said bellows section to be bent with respect to said plunger section.

* * * * *